(12) United States Patent
Parker et al.

(10) Patent No.: US 8,597,454 B2
(45) Date of Patent: Dec. 3, 2013

(54) CATHETER TIP ASSEMBLY

(75) Inventors: Fred T. Parker, Unionville, IN (US); Alexandra E. Jantzen, Durham, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 169 days.

(21) Appl. No.: 13/063,422

(22) PCT Filed: Sep. 18, 2009

(86) PCT No.: PCT/US2009/057443
§ 371 (c)(1),
(2), (4) Date: Jul. 15, 2011

(87) PCT Pub. No.: WO2010/039456
PCT Pub. Date: Apr. 8, 2010

(65) Prior Publication Data
US 2011/0264056 A1 Oct. 27, 2011

Related U.S. Application Data

(60) Provisional application No. 61/099,447, filed on Sep. 23, 2008.

(51) Int. Cl.
*B32B 27/00* (2006.01)
*A61F 2/82* (2013.01)

(52) U.S. Cl.
USPC ........ 156/242; 156/245; 156/294; 156/303.1; 264/523; 264/535; 604/523; 623/1.11

(58) Field of Classification Search
USPC .......................... 264/159, 535; 623/1.11, 1.12
See application file for complete search history.

(56) References Cited

U.S. PATENT DOCUMENTS

| | | | |
|---|---|---|---|
| 4,665,918 A * | 5/1987 | Garza et al. | 606/108 |
| 4,718,423 A | 1/1988 | Willis et al. | |
| 5,334,169 A | 8/1994 | Brown et al. | |
| 6,254,611 B1 | 7/2001 | Vrba | |
| 6,264,683 B1 * | 7/2001 | Stack et al. | 623/1.11 |
| 2001/0037141 A1 | 11/2001 | Yee et al. | |
| 2001/0044629 A1 | 11/2001 | Stinson | |
| 2002/0052641 A1 | 5/2002 | Monroe et al. | |
| 2002/0183826 A1 | 12/2002 | Dorn et al. | |
| 2003/0144671 A1 | 7/2003 | Brooks et al. | |

(Continued)

FOREIGN PATENT DOCUMENTS

| | | |
|---|---|---|
| DE | 3910746 | 10/1990 |
| EP | 0 596 145 A1 | 10/1992 |

(Continued)

*Primary Examiner* — William Bell
(74) *Attorney, Agent, or Firm* — Brinks Gilson & Lione

(57) ABSTRACT

A catheter tip assembly (50) is provided with a catheter tip (56) and an inner catheter (54). The catheter tip (56) has a tapered proximal end, an elongate center portion, and a tapered distal end. The inner catheter (54) includes a narrow proximal portion, a narrow elongate center portion (66), and a wide distal end (68). The catheter tip (56) is disposed within the wide distal end (68) of the inner catheter (54). One advantage of the catheter tip assembly is that no proximal-facing edge is formed at the transition between the narrow elongate center portion of the inner catheter and the catheter tip, which may help reduce the risk of the catheter tip snagging on a stent during use.

9 Claims, 10 Drawing Sheets

(56) References Cited

U.S. PATENT DOCUMENTS

| | | |
|---|---|---|
| 2004/0122415 A1 | 6/2004 | Johnson |
| 2004/0193243 A1* | 9/2004 | Mangiardi et al. ............ 623/1.11 |
| 2005/0060016 A1* | 3/2005 | Wu et al. ....................... 623/1.11 |
| 2006/0253102 A1 | 11/2006 | Nance et al. |
| 2008/0300573 A1* | 12/2008 | Consigny et al. .............. 604/509 |
| 2009/0281610 A1* | 11/2009 | Parker .......................... 623/1.11 |

FOREIGN PATENT DOCUMENTS

| | | |
|---|---|---|
| EP | 0 920 882 A3 | 1/2000 |
| EP | 1 584 305 A2 | 10/2005 |
| EP | 1 767 159 A1 | 3/2007 |
| WO | WO 99/62430 | 12/1999 |
| WO | WO 01/56505 A1 | 8/2001 |
| WO | WO 2004/043301 A1 | 5/2004 |
| WO | WO 2004/103218 A1 | 12/2004 |

* cited by examiner

CATHETER TIP ASSEMBLY

RELATED APPLICATION

This application is a National Stage of International Application No. PCT/US2009/057443 filed on Sep. 18, 2009 with the U.S.P.T.O. as the receiving office, and claims the benefit of U.S. Provisional Application No. 61/099,447 filed on Sep. 23, 2008, the entirety of which are hereby incorporated by reference.

BACKGROUND

The present invention relates generally to medical devices and more particularly to delivery systems for implantable medical devices, such as self-expanding stents.

Stents have become a common alternative for treating vascular conditions because stenting procedures are considerably less invasive than other alternatives. As an example, stenoses in the coronary arteries have traditionally been treated with bypass surgery. In general, bypass surgery involves splitting the chest bone to open the chest cavity and grafting a replacement vessel onto the heart to bypass the stenosed artery. However, coronary bypass surgery is a very invasive procedure that presents increased risk and requires a long recovery time for the patient. By contrast, stenting procedures are performed transluminally and do not require open surgery. Thus, recovery time is reduced and the risks of surgery are minimized.

Many different types of stents and stenting procedures are possible. In general, however, stents are typically designed as tubular support structures that may be inserted percutaneously and transluminally through a body passageway. Typically, stents are adapted to be compressed and expanded between a smaller and larger diameter. However, other types of stents are designed to have a fixed diameter and are not generally compressible. Although stents may be made from many types of materials, including non-metallic materials and natural tissues, common examples of metallic materials that may be used to make stents include stainless steel and nitinol. Other materials may also be used, such as cobalt-chrome alloys, amorphous metals, tantalum, platinum, gold, titanium, polymers and/or compatible tissues. Typically, stents are implanted within an artery or other passageway by positioning the stent within the lumen to be treated and then expanding the stent from a compressed diameter to an expanded diameter. The ability of the stent to expand from a compressed diameter makes it possible to thread the stent through narrow, tortuous passageways to the area to be treated while the stent is in a relatively small, compressed diameter.

Once the stent has been positioned and expanded at the area to be treated, the tubular support structure of the stent contacts and radially supports the inner wall of the passageway. The implanted stent may be used to mechanically prevent the passageway from closing in order to keep the passageway open to facilitate fluid flow through the passageway.

Stents may also be used in combination with other components to treat a number of medical conditions. For example, stent-graft assemblies are commonly used in the treatment of aneurysms. As those in the art well know, an aneurysm is an abnormal widening or ballooning of a portion of an artery. Generally, this condition is caused by a weakness in the blood vessel wall. High blood pressure and atherosclerotic disease may also contribute to the formation of aneurysms. Common types of aneurysms include aortic aneurysms, cerebral aneurysms, popliteal artery aneurysms, mesenteric artery aneurysms, and splenic artery aneurysms. However, it is also possible for aneurysms to form in blood vessels throughout the vasculature. If not treated, an aneurysm may eventually rupture, resulting in internal hemorrhaging. In many cases, the internal bleeding may be so massive that a patient can die within minutes of an aneurysm rupture. For example, in the case of aortic aneurysms, the survival rate after a rupture can be as low as 20%.

Traditionally, aneurysms have been treated with surgery. For example, in the case of an abdominal aortic aneurysm, the abdomen is surgically opened, and the widened section of the aorta is typically dissected longitudinally. A graft material, such as Dacron, is then inserted into the vessel and sutured at each end to the inner wall of the non-widened portions of the vessel. The dissected edges of the vessel may then be overlapped and sutured to enclose the graft material within the vessel. In smaller vessels where the aneurysm forms a balloon-like bulge with a narrow neck connecting the aneurysm to the vessel, the surgeon may put a clip on the blood vessel wall at the neck of the aneurysm between the aneurysm and the primary passageway of the vessel. The clip then prevents blood flowing through the vessel from entering the aneurysm.

An alternative to traditional surgery is endovascular treatment of the blood vessel with a stent-graft. This alternative involves implanting a stent-graft in the blood vessel across the aneurysm using conventional catheter-based placement techniques. The stent-graft treats the aneurysm by sealing the wall of the blood vessel with a generally impermeable graft material.

Thus, the aneurysm is sealed off and blood flow is kept within the primary passageway of the blood vessel. Increasingly, treatments using stent-grafts are becoming preferred since the procedure results in less trauma and faster recuperation.

Self-expanding stents are one common type of stent used in medical procedures. Self-expanding stents are increasingly being used by physicians because of their adaptability to a variety of different conditions and procedures. Self-expanding stents are usually made of shape memory materials or other elastic materials that act like a spring. Typical metals used in this type of stent include Nitinol and stainless steel. However, other materials may also be used.

Traditionally, self-expanding stents have been used in a number of peripheral arteries in the vascular system due to the elastic characteristic of these stents. One advantage of self-expanding stents for peripheral arteries is that traumas from external sources do not permanently deform the stent. As a result, the stent may temporarily deform during unusually harsh traumas and spring back to its expanded state once the trauma is relieved. However, self-expanding stents may be used in many other applications as well.

The above-described examples are only some of the applications in which stents are used by physicians. Many other applications for stents are known and/or may be developed in the future.

To facilitate stent implantation, self-expanding stents are normally installed on the end of an inner catheter in a low profile, compressed state. The distal end of the inner catheter is typically attached to a tapered catheter tip having a lumen. When placed on the inner catheter, the self-expanding stent is positioned just proximal to the catheter tip. The stent is typically inserted into an outer catheter at the end of the catheter, which restrains the stent in the compressed state. The outer catheter is also known as a sheath. The stent and catheter assembly is then guided to the portion of the vessel to be treated. Once the catheter assembly and stent are positioned adjacent the portion to be treated, the stent is released by pulling, or withdrawing, the outer catheter rearward. Normally, a stop member or other feature is provided on the inner catheter to prevent the stent from moving rearward with the outer catheter or sheath. After the stent is released from the retaining outer catheter, the stent springs radially outward to an expanded diameter until the stent contacts and presses against the vessel wall. The inner catheter and attached catheter tip are then withdrawn through the lumen of the stent, leaving the stent in place within the vessel.

As previously noted, in stent delivery systems, the distal end of the inner catheter is attached to a tapered catheter tip. The tapered catheter tip facilitates pushing the stent delivery system through tissue or blood vessels to the desired location. FIG. 1 shows a conventional catheter tip assembly 10 for use in a stent delivery system. As shown in FIG. 1, the catheter tip 12 has a tapered distal end 14, a tapered proximal end 16 and a longitudinally-running lumen 18. The proximal end 16 of the catheter tip 12 is attached to the distal end 20 of the inner catheter 22. The distal end 20 of the inner catheter 22 is sized such that it fits within the proximal portion of the lumen 18 of the catheter tip 12. An adhesive is used to secure the catheter tip 12 to the inner catheter 22. As shown, a stop member 24 may be located on the inner catheter 22, which extends radially outwardly from the inner catheter 22. During use, a self-expanding stent 26 in a compressed state may be loaded on the inner catheter 22 between the stop member 24 and the catheter tip 12.

The manner of attachment between the inner catheter 22 and the catheter tip 12 shown in FIG. 1 poses a risk that the catheter tip 12 will snag or catch the distal end of the self-expanding stent 26 as the inner catheter 22 and catheter tip 12 are withdrawn through the lumen of the expanded stent 26. This is because the juncture between the distal end 20 of the inner catheter 22 and the proximal end 16 of the catheter tip 12 forms an edge 28. This edge 28 may be prone to catching on the stent 26 because it faces the proximal direction. Thus, as the inner catheter 22 and catheter 12 are withdrawn in the proximal direction, the edge 28 may catch on the stent 26. If the catheter tip 12 catches on the stent 26, it may dislodge the stent 26 from the desired location in the patient's body. The catheter tip 12 may also separate from the inner catheter 22 if it catches on the edge of the stent 26, leaving the catheter tip 12 lodged in the vessel where it may block the vessel or cause other complications.

The manner of attachment between the inner catheter 22 and the catheter tip 12 shown in FIG. 1 may also result in the formation of an undesirable gap 34 between a stent 26 loaded on the inner catheter 22 and the stop member 24 on the inner catheter 22. Typically, in conventional systems, the distal end 20 of the inner catheter 22 is threaded through the lumen of a compressed stent 26 and the outer catheter 30 is placed over the compressed stent 26 to prevent it from expanding. After the stent 26 is loaded, the catheter tip 12 is attached to the inner catheter 22, usually with an adhesive. In order to accommodate the process of bonding the inner catheter 22 to the catheter tip 12, a gap 34 may be formed between the stop member 24 and the proximal end 32 of the stent 26. For example, the gap 34 may be between 3 mm and 1 cm in length, as measured in the axial direction. When the outer catheter 30 is withdrawn, the stent 26 initially moves proximally with the retention sheath through the gap 34 until the proximal end 32 of the stent 26 contacts the distal end of the stop member 24. Once the proximal end 32 of the stent 26 contacts the distal end of the stop member 24, the stop member 24 prevents the stent 26 from continuing to move proximally, thereby resulting in relative movement between the outer catheter 30 and the stent 26. However, because the stent 26 initially moves proximally with the outer catheter 30 through the gap 34, a slight delay in deployment may occur. This delay in deployment may cause inaccuracy in placement of the stent.

SUMMARY

A catheter tip assembly having a catheter tip that rests in a flared distal portion of an inner catheter is described. The catheter tip has a tapered proximal end, an elongate center portion, and a tapered distal end. The inner catheter includes a narrow proximal portion, a narrow elongate center portion, and a wide distal end. The inner catheter flares outwardly from the narrow elongate center portion of the inner catheter to form the wide distal end of the inner catheter. The proximal end of the catheter tip and at least a portion of the elongate center portion of the catheter tip are disposed in the wide distal end of the inner catheter. One advantage of having a catheter tip that rests in a wide distal portion of an inner catheter is that there is no proximal-facing edge formed at the juncture of the inner catheter and the catheter tip that may catch on a stent as the inner catheter is withdrawn in the proximal direction through the lumen of an expanded stent.

One embodiment of a catheter tip assembly comprises: a catheter tip having a tapered proximal end, an elongate center portion, and a tapered distal end; and an inner catheter including a narrow proximal portion, a narrow elongate center portion having a first outer diameter and a first inner diameter, and a wide distal end ending with a distal edge, the wide distal end having a second outer diameter and a second inner diameter at the distal edge, wherein the inner catheter flares outwardly from the narrow elongate center portion of the inner catheter to form the wide distal end of the inner catheter and the second inner diameter is greater than the first inner diameter, wherein the tapered proximal end of the catheter tip and at least part of the elongate center portion of the catheter tip are disposed in the wide distal end of the inner catheter.

Another embodiment comprises a catheter tip assembly wherein the second inner diameter of the inner catheter is at least approximately between two to five times greater than the first inner diameter of the inner catheter.

Another embodiment comprises a catheter tip assembly wherein the narrow elongate center portion of the inner catheter has a first thickness comprising one half of the difference between the first inner diameter and the first outer diameter, the wide distal end of the inner catheter has a second thickness at the distal edge comprising one half of the difference between the second inner diameter and the second outer diameter, and the first thickness is greater than the second thickness.

Another embodiment comprises a catheter tip assembly wherein the transition between the first thickness of the inner catheter and the second thickness of the inner catheter is gradual.

Another embodiment comprises a catheter tip assembly wherein the first thickness of the inner catheter is approximately 10 thousandths of an inch and the second thickness of the inner catheter is approximately 5 thousandths of an inch.

Another embodiment comprises a catheter tip assembly wherein the inner catheter is polyethylene terephthalate.

Another embodiment comprises a catheter tip assembly further comprising an outer catheter defining a lumen, wherein the inner catheter is disposed coaxially within the lumen of the outer catheter.

Another embodiment comprises a catheter tip assembly further comprising a stent defining a lumen, wherein the stent is disposed coaxially within the lumen of the outer catheter and the inner catheter is disposed coaxially within the lumen of the stent.

Another embodiment comprises a catheter tip assembly further comprising a stop member disposed on the inner catheter proximal to the narrow proximal portion of the inner catheter, wherein the stop member extends radially outwardly from the inner catheter.

Another embodiment comprises a catheter tip assembly wherein the stop member is integral with the inner catheter.

Another embodiment of a catheter tip assembly comprises: a catheter tip having a tapered proximal end, an elongate center portion, and a tapered distal end; an outer catheter defining a first lumen; a compressed stent disposed coaxially within the first lumen, the compressed stent defining a second lumen, the stent having a proximal end and a distal end; and an inner catheter disposed coaxially within the second lumen, the inner catheter including a narrow proximal portion, a stop member extending radially outwardly from the inner catheter proximal to the narrow proximal portion, a narrow elongate center portion having a first outer diameter and a first inner diameter, and a wide distal end ending with a distal edge, the wide distal end having a second outer diameter and a second inner diameter at the distal edge; wherein the inner catheter flares outwardly from the narrow elongate center portion of the inner catheter to form the wide distal end of the inner catheter and the second inner diameter is greater than the first inner diameter, wherein the tapered proximal end of the catheter tip and at least part of the elongate center portion of the catheter tip are disposed in the wide distal end of the inner catheter, wherein the proximal end of the stent abuts the stop member and the distal end of the stent abuts the wide distal end of the inner catheter.

Another embodiment comprises a method for making a catheter tip assembly comprising: providing a catheter tip having an inner diameter defining a lumen and a greatest outer diameter, the catheter tip having a tapered proximal end, an elongate center portion, and a tapered distal end; providing a first tubular body having a longitudinal axis, and an inner diameter slightly greater than the greatest outer diameter of the catheter tip; placing a second tubular body coaxially within the first tubular body, the second tubular body having an inner diameter defining a lumen and an outer diameter; positioning the second tubular body within the first tubular body so that the second tubular body is at least approximately centered within the first tubular body; blow molding a portion of the second tubular body until a greatest outer diameter of the blow-molded portion of the second tubular body is approximately equal to the inner diameter of the first tubular body; removing the second tubular body from the first tubular body; severing the second tubular body laterally to the longitudinal axis along the blow-molded portion, thereby forming a narrow elongate portion and a blow-molded wide distal end having a distal edge; applying an adhesive to the tapered proximal end of the catheter tip; and placing the catheter tip into the lumen of the wide distal end of the second tubular body.

Another embodiment of a method for making a catheter tip assembly further comprises: threading a mandrel through the lumen of the second tubular body and the lumen of the catheter tip; and heating the second tubular body to at least approximately the glass transition temperature of the second tubular body;

Another embodiment of a method for making a catheter tip assembly further comprises shaping the distal edge of the wide distal end so that the distal edge is tapered.

Another embodiment of a method for making a catheter tip assembly further comprises heating and shaping generally simultaneously.

Another embodiment of a method for making a catheter tip assembly further comprises applying a compressive force to the wide distal end of the second tubular body, thereby compressing the wide distal end around the catheter tip.

Another embodiment of a method for making a catheter tip assembly further comprises severing the second tubular body at approximately the greatest outer diameter of the blow-molded portion of the second tubular body.

Another embodiment of a method of making a catheter tip assembly further comprises thinning a portion of the second tubular body prior to blow molding.

Another embodiment of a method for making a catheter tip assembly comprises blow molding which comprises: sealing an end of the second tubular body; blowing pressurized air through the second tubular body; heating a portion of the second tubular body to a temperature at least approximately the glass transition temperature of the second tubular body; and allowing the second tubular body to cool.

Another embodiment of a method for making a catheter tip assembly comprises: providing a catheter tip having an inner diameter defining a lumen and a greatest outer diameter, the catheter tip having a tapered proximal end, an elongate center portion, and a tapered distal end; providing a first tubular body having a longitudinal axis, and an inner diameter slightly greater than the greatest outer diameter of the catheter tip; compressing a stent having a distal end and a proximal end, the stent being shorter than the first tubular body; placing the compressed stent coaxially within the first tubular body; placing a second tubular body comprised of a blow-moldable material coaxially within the stent, the second tubular body being longer than the stent; positioning the second tubular body and the compressed stent within the first tubular body so that the second tubular body is at least approximately centered within the first tubular body; blow molding a first portion of the second tubular body that is distal to the stent until a greatest outer diameter of the blow-molded first portion of the second tubular body is at least approximately equal to the inner diameter of the first tubular body; blow molding a second portion of the second tubular body that is proximal to the stent until a greatest outer diameter of the blow-molded second portion of the second tubular body is at least approximately equal to the inner diameter of the first tubular body; severing the second tubular body laterally to the longitudinal axis along the first blow-molded portion, thereby forming a blow-molded wide distal end having a distal edge, the wide distal end defining a lumen; severing the second tubular body laterally to the longitudinal axis along the second blow-molded portion, thereby forming a blow-molded wide proximal end having a proximal edge, the wide proximal end defining a lumen having a second inner diameter; transferring the stent and the blow-molded second tubular body from the first tubular body into an outer catheter; maintaining the stent in a compressed state as it is transferred from the first tubular body into the outer catheter; applying an adhesive to at least a portion of the tapered proximal end of the catheter tip; placing the catheter tip into the lumen of the wide distal end of the second tubular body; applying adhesive to an exterior portion of an end of a piece of tubing, the piece of tubing having an outer diameter that is slightly less than the inner diameter of the lumen of the wide proximal end of the second tubular body; and inserting the end of the piece of tubing into the lumen of the wide proximal end of the second tubular body The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION OF THE DRAWINGS AND THE PRESENTLY PREFERRED EMBODIMENTS

Figure 1:
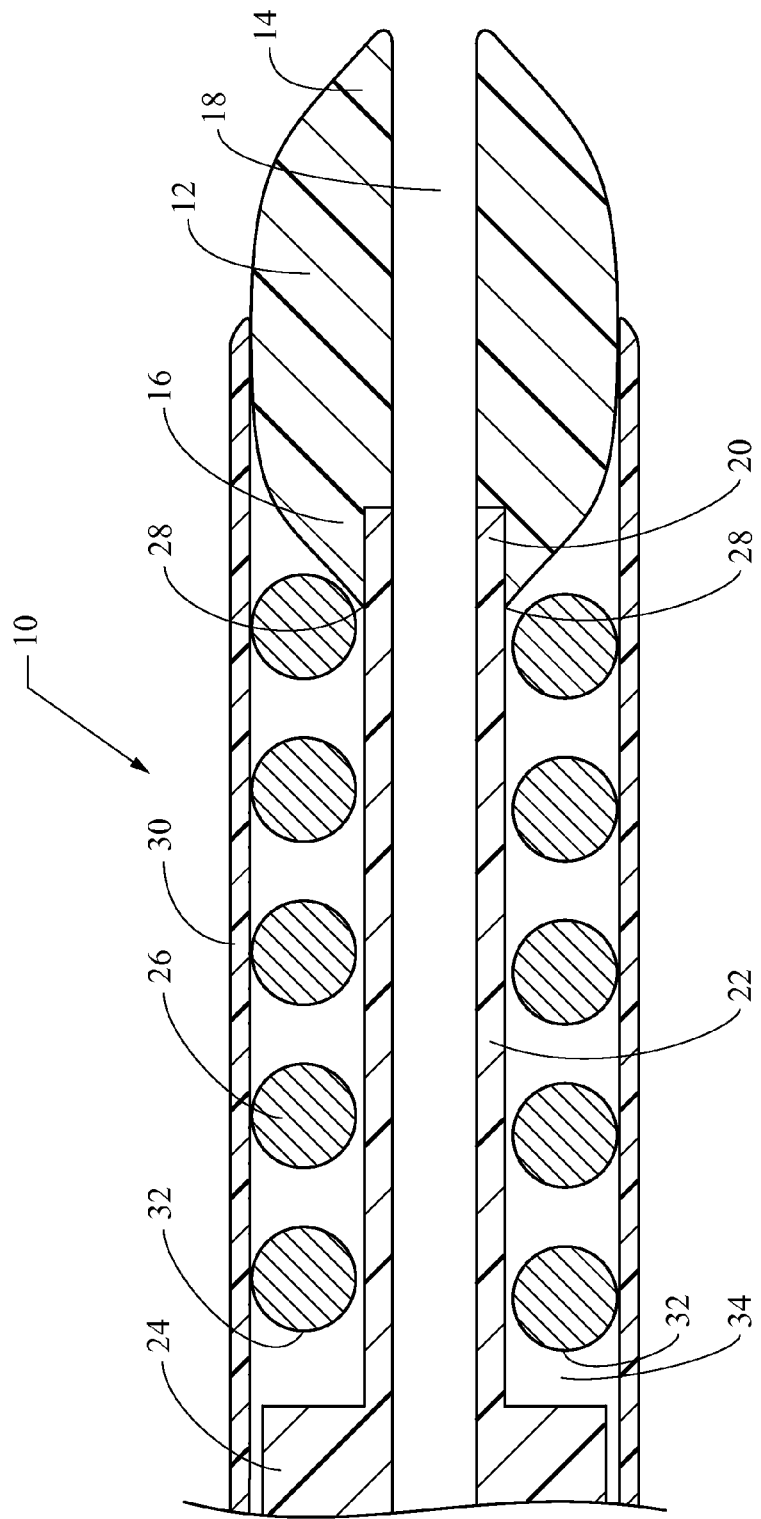
FIG. 1 is a partial side cross-sectional view of a conventional catheter tip assembly.
Figure 2A:
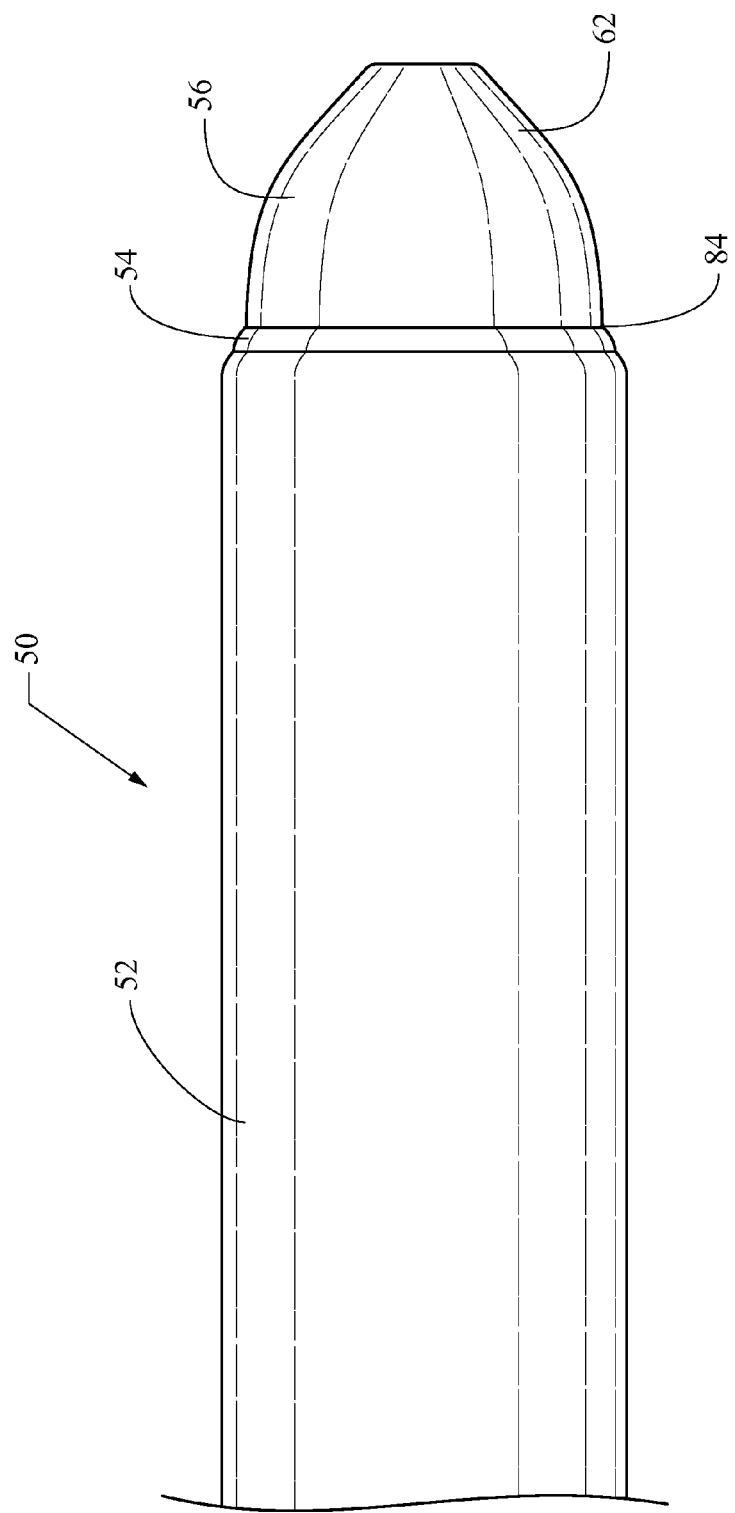
FIG. 2A is a partial side view of a catheter tip assembly.

Referring now to the drawings, and particularly to FIG. 2A, a catheter tip assembly 50 is shown. In the present application, the term "proximal" refers to the direction that is generally toward a physician during a medical procedure, while the term "distal" refers to the direction that is generally towards a target site within a patient's anatomy during a medical procedure.

Figure 2B:
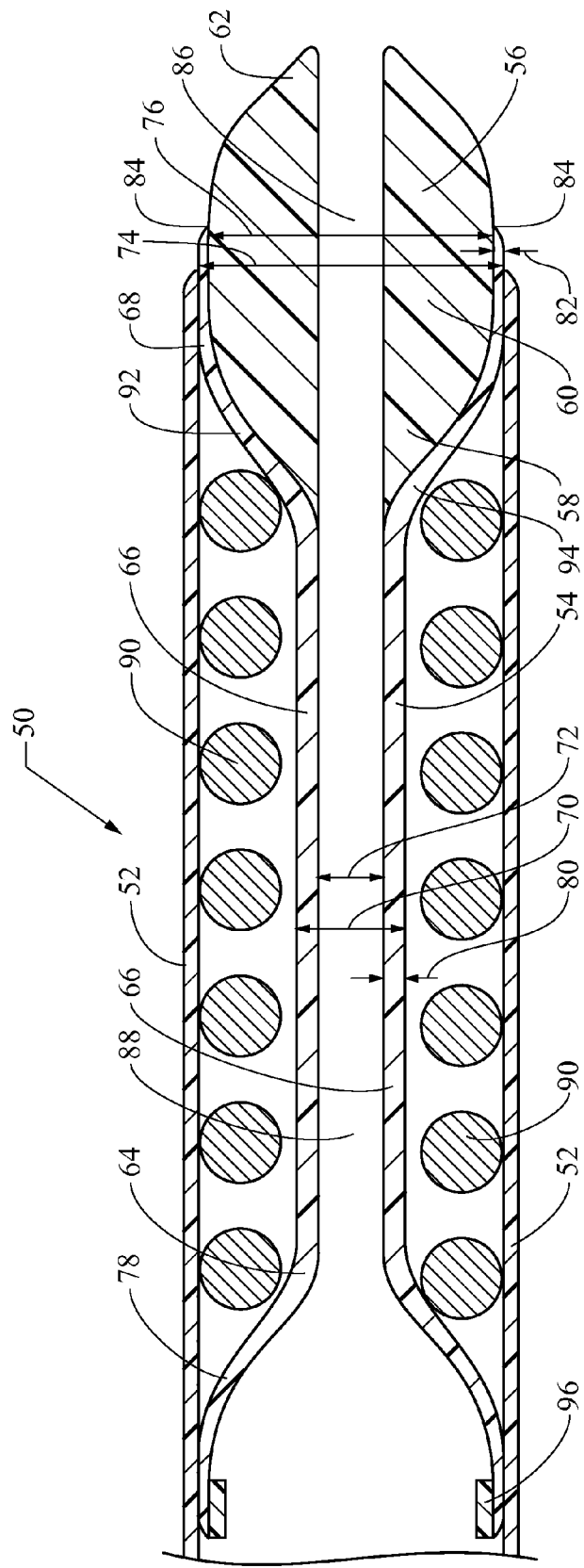
FIG. 2B is a side cross-sectional view of the catheter tip assembly of FIG. 2A.

As shown in FIGS. 2A and 2B, the catheter tip assembly 50 may include an outer catheter 52, an inner catheter 54, and a catheter tip 56. As best shown in FIG. 2B, the catheter tip 56 includes a tapered proximal end 58, an elongate center portion 60, and a tapered distal end 62. The inner catheter 54 of the catheter tip assembly 50 includes a narrow proximal portion 64, a narrow elongate center portion 66, and a wide distal end 68 ending with a distal edge 84. The inner catheter 54 flares outwardly from the narrow elongate center portion 66 to form the wide distal end 68. The narrow elongate center portion 66 defines a first outer diameter 70 and a first inner diameter 72 of the catheter tip assembly 50. The wide distal end 68 of the inner catheter 54 defines a second outer diameter 74 and second inner diameter 76. The second outer diameter 74 and second inner diameter 76 are determined by measuring the wide distal end 68 of the inner catheter 54 at approximately the distal edge 84, as shown in FIG. 2B. The second inner diameter 76 is greater than the first inner diameter 72.

FIG. 2B also illustrates that the proximal end 58 of the catheter tip 56 and a portion of the elongate center portion 60 of the catheter tip 56 are disposed in the wide distal end 68 of the inner catheter 54. The embodiment shown in FIGS. 2A and 2B also illustrates that the inner catheter 54 and the catheter tip 56 may be disposed coaxially within an outer catheter 52.

FIG. 2B illustrates additional features that may be present is some preferred embodiments. As shown in FIG. 2B, the catheter tip assembly 50 may include a stop member 78 located on the inner catheter 54. The stop member 78 is located proximally to the wide distal end 68 of the inner catheter 54. The distance between the stop member 78 and the wide distal end 68 is preferably configured to allow a stent 90 to fit between the stop member 78 and the wide distal end 68 of the inner catheter 54. It is preferable that the stent 90 abut the stop member 78 and the flared portion 92 of the wide distal end 68 of the inner catheter 54. However, in some embodiments, the stent will not abut the stop member 78 or the flared portion 92 of the wide distal end 68 of the inner catheter 54. The stop member may be integral with the inner catheter 54 as shown in FIG. 2B or a separate piece attached to the inner catheter 54. In embodiments having an integral stop member 78, it may be preferably to connect a separate piece of tubing 96 to the end of the inner catheter for purposes of threading the catheter tip assembly 50 into a patient. Any stop member known in the art may be used.

As shown in FIG. 2B, some embodiments may feature an inner catheter 54 that varies in thickness. The elongate center portion 66 of the inner catheter 54 has a first thickness 80. The first thickness 80 comprises one half of the difference between the first inner diameter 72 and the first outer diameter 70 of the inner catheter 54. The wide distal end 68 of the inner catheter 54 has a second thickness 82. This second thickness 82 comprises one half of the difference between the second inner diameter 76 and the second outer diameter 74. The first thickness 80 is greater than the second thickness 82 in the embodiment shown in FIG. 2B. Thus, in this embodiment, the thickness of the inner catheter 54 is generally greater along the elongate center portion 66 than along the wide distal end 68. The thickness value may vary depending on the original thickness of the inner catheter prior to blow molding. After blow molding, the first thickness is preferably about two times the second thickness. In one preferred embodiment, the first thickness is approximately 10 thousandths of an inch and the second thickness is approximately 5 thousandths of an inch. In another preferred embodiment the first thickness is approximately 60 thousandths of an inch and the second thickness is approximately 35 thousandths of an inch. However, any other thickness known in the art may be used.

Having an inner catheter that is thicker along the narrow elongate center portion and thinner along the wide distal end may be advantageous because, in embodiments with this feature, the wide distal end adds only a minimal amount of width to the catheter tip. Thus, the overall diameter of the catheter-tip assembly does not have to be increased substantially to accommodate the wide distal end of the inner catheter. Moreover, if the outer diameter of the catheter tip is decreased slightly, it is possible that the catheter tip assembly could accommodate a stent of the same size as a conventional catheter tip assembly without any increase in the overall maximum diameter of the catheter tip assembly. It is also advantageous to have an inner catheter that has a greater thickness along the elongate center portion than the wide distal end because this ensures that the elongate center portion has the maximum amount of strength possible. Although it may be advantageous to have a catheter tip assembly having a greater thickness along the elongate center portion than the wide distal end, in other embodiments, the thickness of the inner catheter along the elongate center portion may be less than the thickness along the wide distal end. In still other embodiments, the thickness of the inner catheter may be substantially the same throughout the length of the inner catheter.

It is also preferable that the wide distal end 68 of the inner catheter 53 have a thickness that decreases gradually from the proximal end 94 of the wide distal end 68 to the distal edge 84. Thus, the thickness of the inner catheter 54 at the wide distal edge 84 will be less than the thickness of the inner catheter 54 at the proximal end 94 of the wide distal end 68. This may be advantageous because it spreads out the transition between the inner catheter 54 and the catheter tip 56 over a greater length of material. Stress points tend to form at the interfaces between two different materials, e.g., the interface between the inner catheter and the catheter tip 56. By creating a transition over a long area, the gradual tapering of the wide distal end 68 decreases the possibility of a stress point forming at the distal edge 84 and increases the catheter tip assembly's 50 resistance to kinking when bent. In order to make an even more gradual transition at the interface between the inner catheter and the catheter tip 56, an adhesive may be applied at the juncture between the distal edge 84 and the catheter tip 56 after the catheter tip 56 is in place. Suitable adhesives include cyanoacrylates such as superglue or UV light curing adhesives. Any type of suitable adhesive known in the art may be used.

The inner catheter 54 of the embodiment shown in FIGS. 2A and 2B has a distal edge 84. As shown in FIGS. 2A and 2B, the distal edge 84 of the inner catheter is preferably tapered and rounded. This may prevent the distal edge 84 from snagging on tissue or otherwise injuring a patient during use. It also forms a smooth transition between the catheter tip 56 and the outer catheter 52 to facilitate insertion into a patient. Although embodiments with a distal edge 84 that is both tapered and rounded may be advantageous, other embodiments may have a distal edge that is blunt, rounded only, or tapered only. The distal end of the inner catheter may also have any other shape or form known in the art.

The inner catheter 54 and the catheter tip 56 are preferably bonded together through the use of an adhesive. The adhesive is preferably fast-drying, and even more preferably a cyanoacrylate such as superglue. Although cyanoacrylates are a preferred embodiment, any type of adhesive known in the art may be used. The adhesive is preferably placed along at least part of the tapered proximal end 58 of the catheter tip 56. As the catheter tip 56 is inserted into the wide distal end 68 of the inner catheter 54, the adhesive is skimmed by the inner surface of the wide distal end 68, thereby causing the glue to be applied in a fairly uniform thickness. An adhesive may be applied to any point of contact between the inner surface of the wide distal end 68 and the catheter tip 56. The glue preferably bonds together most, if not all, of the surface of the catheter tip 56 that contacts the inner surface of the wide distal end 68 of the inner catheter 54. Because there is a fairly large surface area of the inner catheter 54 that contacts the catheter tip 56, a strong bond may be formed between the catheter tip 56 and the inner catheter 54. This bond may prevent the catheter tip 56 from breaking free of the inner catheter 54 during a medical procedure. Although some preferred embodiments utilize an adhesive, other embodiments will not utilize an adhesive to bond the inner catheter and the catheter tip. In embodiments without an adhesive, interlocking components, threading, snaps, a tight fit, or any other method of attaching two component parts known in the art may be used to bond the inner catheter and catheter tip together.

The amount of difference in diameter between the wide distal end 68 of the inner catheter 54 and the narrow elongate center portion 66 of the inner catheter 54 may vary. In some embodiments the inner diameter 76 of the wide distal end 68 of the inner catheter 54 may be at least approximately between two to five times greater than the inner diameter 72 of the elongate center portion 66 of the inner catheter 54. In other embodiments, the difference between the inner diameter 76 of the wide distal end 68 and the elongate center portion 66 may not be so great. For example, the inner diameter 76 of the wide distal end 68 of the embodiment shown in FIG. 2B is approximately three times greater than the inner diameter 72 of the elongate center portion 66 of the inner catheter 54.

In the embodiment shown in FIG. 2B, the diameter of the lumen 86 of the catheter tip 56 is approximately equal to the first inner diameter 72 of the inner catheter 54. This may be advantageous because a single continuous lumen is formed by the lumen 86 of the catheter tip 56 and the lumen 88 of the inner catheter 54. However, in other embodiments the diameter of the lumen 86 of the catheter tip 56 may be different than the first inner diameter 72 of the inner catheter 54. In embodiments in which the diameter of the lumen 86 and the first inner diameter 72 vary, it is preferable that the diameter of the lumen 86 of the catheter tip 56 be slightly larger than the first inner diameter 72 of the inner catheter 54. However, in other embodiments, the diameter of the lumen 86 of the catheter tip 56 may be smaller than the first inner diameter 72.

The embodiment shown in FIGS. 2A and 2B may be used to insert a self-expanding stent 90 into a blood vessel of a patient. The inner catheter 54 may be threaded through the lumen of a self-expanding stent 90 so that the stent 90 is located between the wide distal end 68 of the inner catheter 54 and the stop member 78. The stent 90 is compressed before the stent 90 and inner catheter 54 are placed within the lumen of the outer catheter 52. The self expanding stent 90 typically presses outward against the inner surface of the outer catheter 52, thereby producing a small amount of friction between the stent 90 and the retention outer catheter 52.

The insertion of the catheter tip assembly 50 with the stent 90 into a body may be accomplished using the Seldinger technique. During insertion, the components of the catheter tip assembly 50 are positioned so that the catheter tip 56 protrudes from the distal end of the outer catheter 52 as shown in FIGS. 2A and 2B. It is also preferable that the distal edge 84 of the inner catheter 54 protrude slightly from the distal end of the outer catheter 52. This creates a smooth transition between the catheter tip 56 and the outer catheter 52. It also prevents the formation of a gap between the catheter tip 62 and the outer catheter 52 that might allow blood, tissue, or fluids to seep into the catheter tip assembly 50.

Once the catheter tip assembly 50 is positioned at the desired location in a blood vessel, the stent 90 may be released from the delivery system by withdrawing the outer catheter 52 proximally relative to the inner catheter 54. However, the stop member 78 prevents the stent 90 from moving proximally with the outer catheter 52 as the outer catheter 52 is withdrawn. In effect, the stent 90 is pushed out of the outer catheter 52 by the stop member 78 as the outer catheter 52 is withdrawn. The stent 90 expands once it becomes free of the outer catheter 52. Once the expanded stent 90 is in place within the vessel, the inner catheter 54 and catheter tip 56 are withdrawn through the lumen of the stent 90. The transition between the narrow elongate center portion 66 of the inner catheter 54 and the wide distal end 68 of the inner catheter 54 lacks a proximal-facing edge. Instead, the distal edge 84 faces the distal direction. This may be advantageous because it reduces the risk that the catheter tip 56 will catch on or snare the stent 90 as the inner catheter 54 and the catheter tip 56 are moved in the proximal direction through the lumen of the stent 90. This prevents the catheter tip 56 from dislodging the stent 90 from the desired location in the patient during removal of the catheter tip 56. It is also advantageous because it reduces the risk that the catheter tip 56 will snare on the stent 90 and become detached from the inner catheter 54.

The catheter tip assembly 50 may have radiopaque qualities to facilitate the location of the device during an operation. A radiopaque marker may be placed in the catheter tip 56 to facilitate location of the tip. The distal end of the outer catheter may also contain a radiopaque material such as a loop of tungsten. The use of radiopaque materials at the distal end of the outer catheter may facilitate placing the catheter-tip assembly in the desired location within a patient. Finally, the stent itself may be radiopaque to facilitate placement. Any other portion of the catheter tip assembly may have radiopaque qualities. In addition, any other device useful for locating the catheter tip assembly 50 during an operation may be used.

The catheter tip 56 may be made of any biocompatible material. The tip is preferably composed of a material having a low durometer such as nylon, polyurethanes, vinyls, or polyvinyls (e.g., polyvinyl chloride (PVC)). The catheter tip may be composed of any such material or a combination thereof. It may be advantageous to utilize a flexible material for the catheter tip because this may allow the catheter tip to bend and weave through blood vessels to reach the desired location within the patient's body. However, the catheter tip may also be composed of materials that do not have a low durometer.

The inner catheter is preferably composed of any blow-moldable material such as polyethylene terephthalate (PET) or PVC. Any other biocompatible and blow-moldable material known in the art may be used. The outer catheter may be composed of polyetheretherketone (PEEK), PVC, Flexor®, or any other suitable biocompatible material known in the art. The inner catheter may be connected to a tube of relatively rigid material such as PEEK.

For some embodiments, it may be advantageous to utilize the same material for both the catheter tip and the inner catheter. For example, the inner catheter and the catheter tip may both be composed of PVC. This may be advantageous because both components will have the same bonding affinity to any given adhesive, making it easier to find a workable adhesive.

In other embodiments it may be advantageous to utilize two different materials for the catheter tip and the inner catheter. This may allow the user to select materials with properties particularly suited for different uses. For example, a material with an optimal durometer may be used for the catheter tip and a different material with optimal blow molding properties may be used for the inner catheter.

Figure 3A:
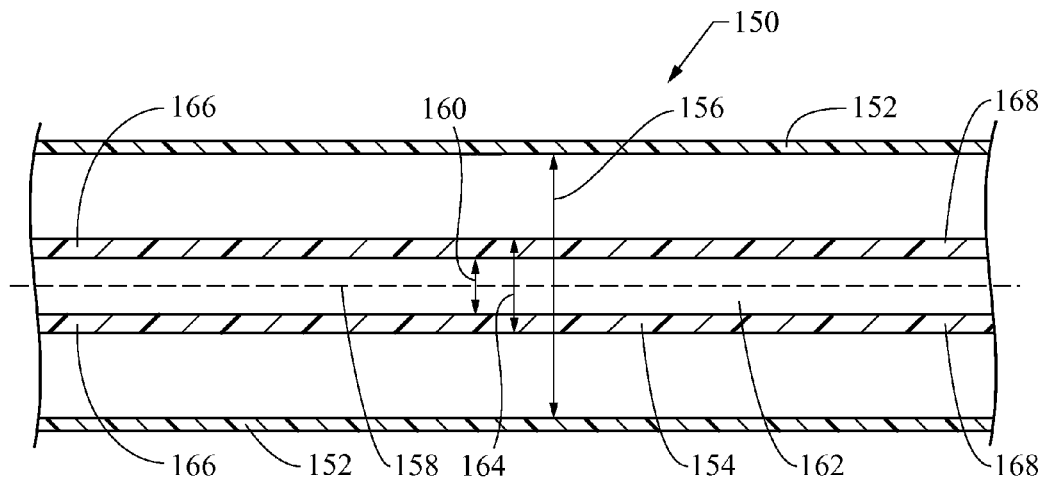
FIG. 3A is a partial side cross-sectional view of a first and second tubular body of a blow-molding assembly.
Figure 3B:
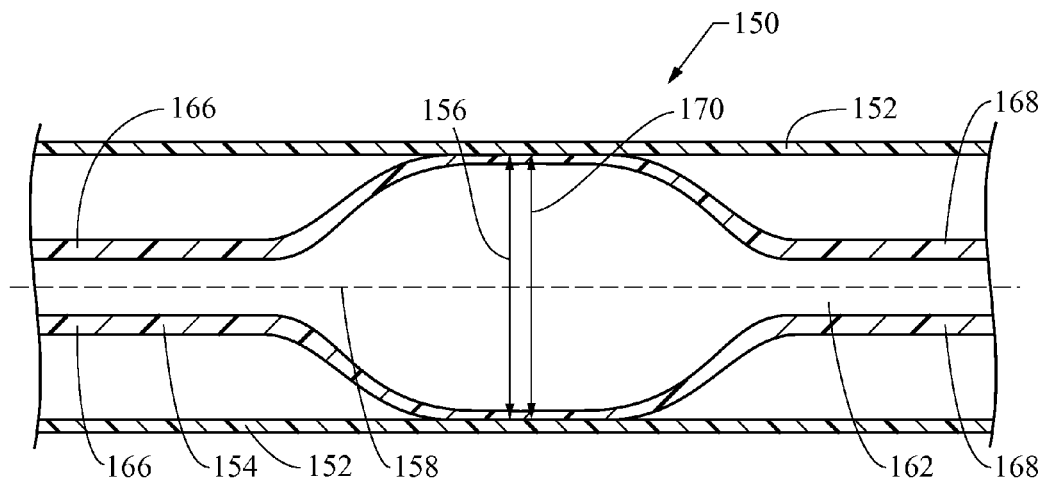
FIG. 3B is a partial side cross-sectional view of a first and second tubular body of the blow-molding assembly of FIG. 3A after blow molding.
Figure 3C:
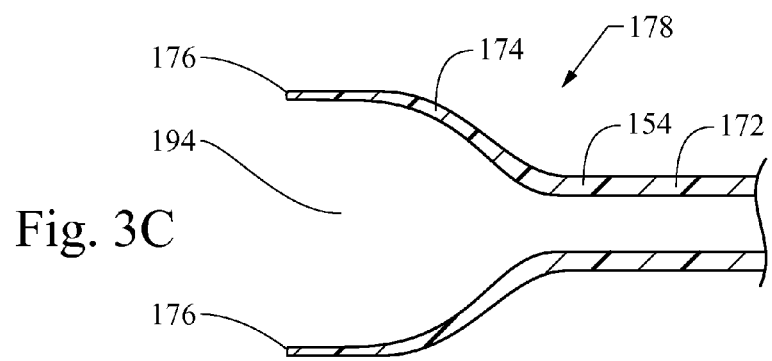
FIG. 3C is a partial side cross-sectional view of an inner catheter formed by the blow-molding assembly of FIG. 3B.
Figure 3D:
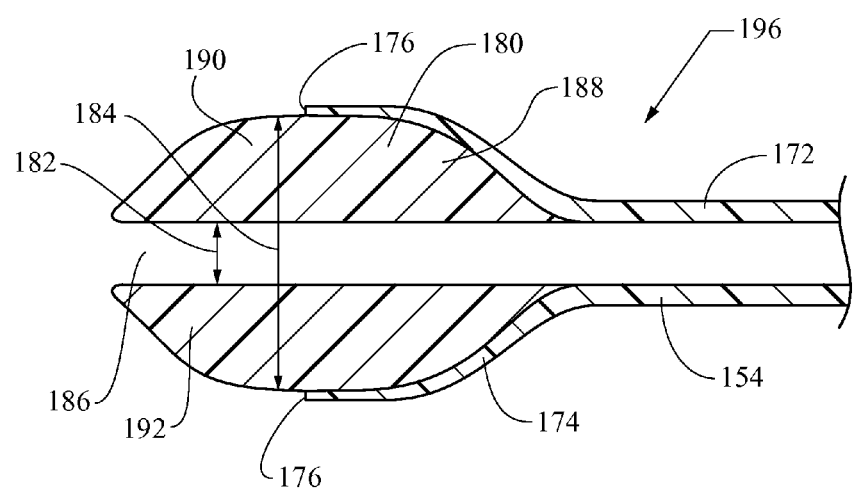
FIG. 3D is a partial side cross-sectional view of a catheter tip assembly.
Figure 3E:
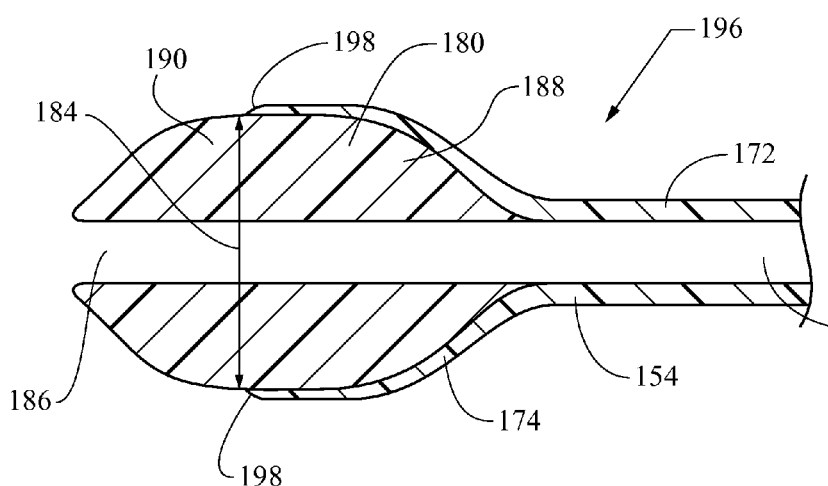
FIG. 3E is a partial side cross-sectional view of a catheter tip assembly.
Figure 3F:
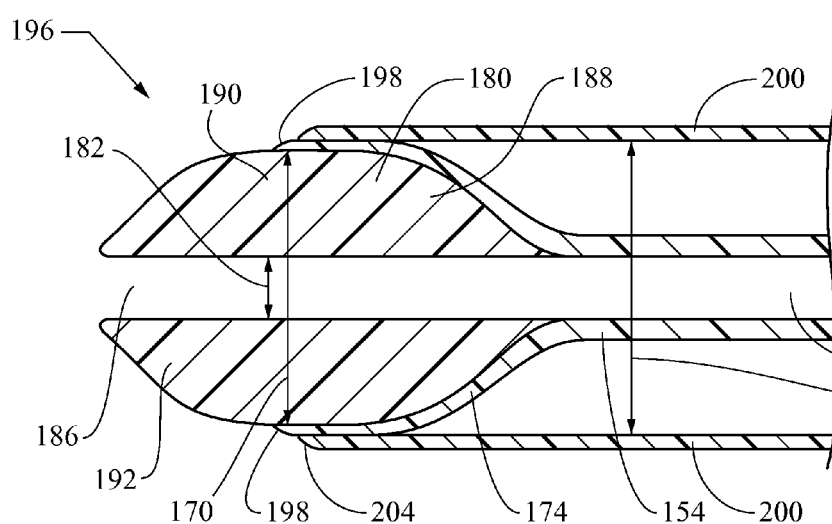
FIG. 3F is a partial side cross-sectional view of a catheter tip assembly.
Figure 4:
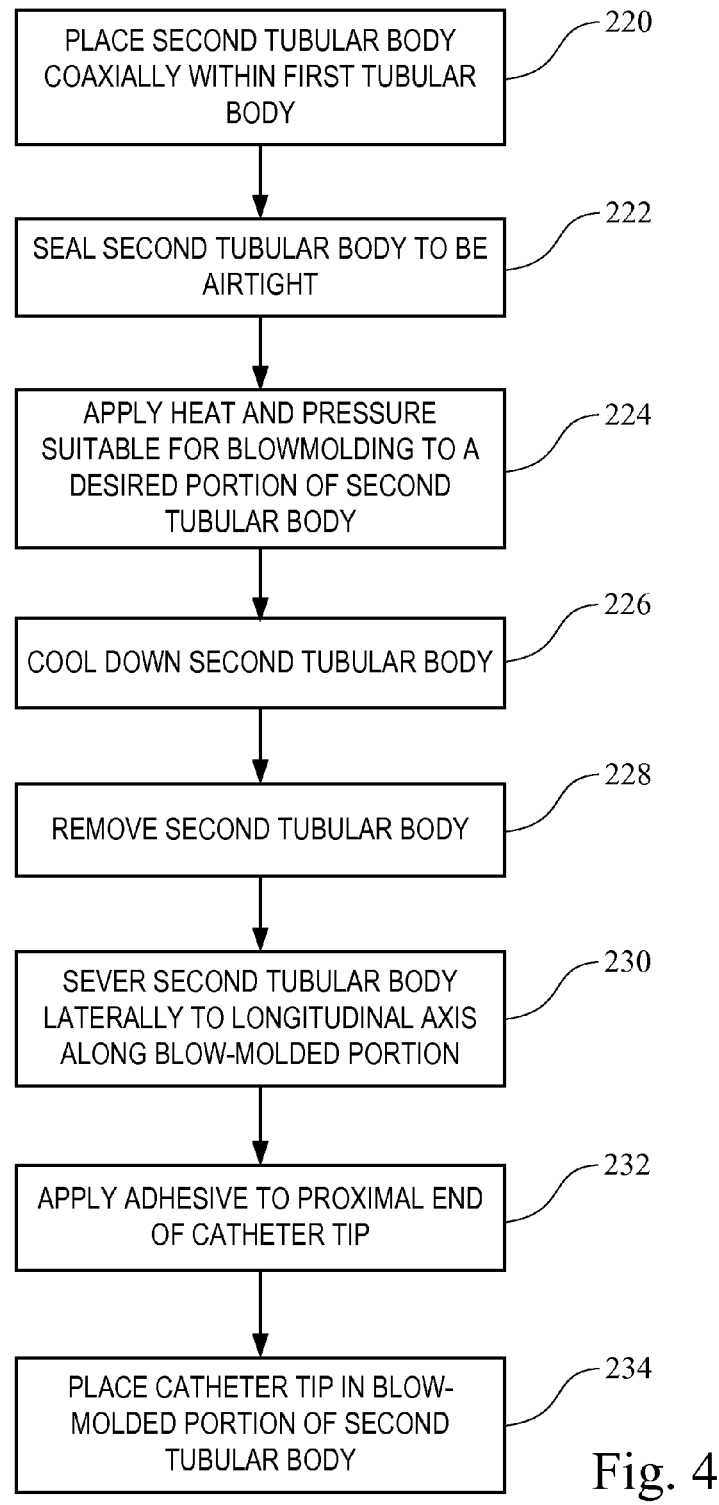
FIG. 4 illustrates an embodiment of a method for forming a catheter tip assembly.

FIGS. 3A-F, and FIG. 4 show a method for making a catheter tip assembly. FIG. 4 shows generally the steps of making a catheter tip assembly. FIGS. 3A-F illustrate a blow molding assembly 150 and catheter tip assembly 178 during the process of making the catheter tip assembly. As set forth in FIG. 4, in one embodiment, the second tubular body may be placed coaxially within the first tubular body (Act 220). The second tubular body is sealed to be airtight (Act 222). Heat and pressure suitable for blow molding are applied to a desired portion of the second tubular body (Act 224). The second tubular body is cooled and then removed from the first tubular body (Act 226). The second tubular body is severed laterally to the longitudinal axis along the blow-molded portion of the second tubular body (Act 228). In the alternative, the second tubular body may be removed (Act 228) after it is severed (Act 230). One or both halves of the severed second tubular body may be suitable for a catheter tip assembly (Act 230). An adhesive is then applied to the proximal end of a catheter tip (Act 232) and the catheter tip is placed in the blow molded portion of a suitable half of the severed second tubular body to form a catheter tip assembly (Act 234).

FIGS. 3A-F illustrate in greater detail a method for making a catheter tip assembly 196. FIG. 3F shows a catheter tip assembly 196 made according to this method. As shown in FIG. 3A, a catheter tip assembly 196 may be made with a first tubular body 152, and a second tubular body 154. The size and dimensions of the first tubular body 152 and second tubular body 154 shown in FIG. 3A are adjusted to work with the catheter tip 180 shown in FIG. 3F. The catheter tip 180 has an inner diameter 182 that defines a lumen 186, a greatest outer diameter 184, a tapered proximal end 188, an elongate center portion 190, and a tapered distal end 192. The greatest outer diameter 184 of the catheter tip 180 is the diameter of the catheter tip 180 at its widest point.

FIG. 3A shows a blow-molding assembly 150 suitable for making the catheter tip assembly 196 of FIG. 3F. As shown in FIG. 3A, the first tubular body 152 has a longitudinal axis 158 and an inner diameter 156 that is slightly greater than the greatest outer diameter 184 of the catheter tip 180. As shown in FIG. 3A, the second tubular body 154 has an inner diameter 160 that defines a lumen 162 and an outer diameter 164.

FIG. 3A illustrates that the second tubular body 154 may be placed coaxially within the first tubular body 152. The second tubular body 154 is preferably positioned so that it is at least approximately centered within the first tubular body 152. When centered, the central longitudinal axis of the second tubular body 154 is the same as the central longitudinal axis 158 of the first tubular body 152.

Once the two tubular bodies are positioned as shown in FIG. 3A, they form a blow molding assembly 150. The second tubular body 154 of the blow molding assembly 150 may be blow molded to the desired shape. Blow molding may be accomplished by sealing a first end 166 of the second tubular body 154. Pressurized air may then be blown into a second end 168 of the second tubular body 154. Heat is then applied to a portion of the second tubular body 154 at a temperature approximately equal to the glass transition temperature of the second tubular body 154. The desired portion of the second tubular body 154 is blow molded until the greatest outer diameter 164 of the blow-molded portion of the second tubular body 154 is approximately equal to the inner diameter 156 of the first tubular body 152. Once the second tubular body 154 has been blow molded to the desired shape, the second tubular body 154 may be allowed to cool. Until the second tubular body 154 is completely cooled, it is preferable that the pressurized air flow be maintained to reduce the risk of the blow-molded portion of the second tubular body 154 reverting to its original shape. Cooling to room temperature is often sufficient. However, the temperature required for cooling may vary depending on the material composition of the second tubular body.

FIG. 3B illustrates the first 152 and second tubular bodies 154 after blow molding is complete. As shown, a portion of the second tubular body 154 is much wider than the rest of the second tubular body 154. The greatest outer diameter 170 of the second tubular body 154 is measured at the widest portion of the blow-molded portion of the second tubular body 154. As shown in FIG. 3B, it is preferable that the greatest outer diameter 170 is approximately equal to the inner diameter 156 of the first tubular body 152.

After the blow molding is completed, the second tubular body 154 may be removed from the first tubular body 152. The second tubular body may then be severed laterally to the longitudinal axis 158 of the second tubular body 154 along the blow-molded portion to form a narrow elongate portion 172 and a blow-molded wide distal end 174 having a distal edge 176. FIG. 3C illustrates the second tubular body 154 after being severed in the manner described. The method shown in FIGS. 3B and 3C shows the removal of the second tubular body before severing. However, this step may also be performed after the second tubular body is severed.

The embodiment shown in FIG. 3C resulted from severing the embodiment shown in FIG. 3B along the greatest outer diameter 170 of the blow-molded portion. It may be preferable to sever the second tubular body 154 along the widest portion because this will often allow both halves of the second tubular body 154 to be utilized to form two separate catheter tip insertion assemblies. Although it may be preferable to sever the second tubular body 154 along the greatest outer diameter 170 of the blow-molded portion, the second tubular body 154 may also be severed at any other place along the blow-molded portion. Once severed, at least one of the two remaining portions of the second tubular body 154 may serve as an inner catheter 178.

FIG. 3D illustrates a catheter tip assembly 196 formed by the insertion of a catheter tip 180 into the lumen 194 of the wide distal end 174 of the second tubular body 154. The catheter tip 180 may be bonded to the second tubular body 154 by applying an adhesive to the tapered proximal end 188 of the catheter tip 180. The catheter tip 180 may then be placed in the lumen 194 of the wide distal end of the second tubular body 154.

As shown in FIG. 3E, the distal edge 176 of the second tubular body 154 may be shaped in some embodiments so that it is tapered and rounded. FIG. 3E shows a tapered, rounded distal edge 198. This tapering may be accomplished by threading a mandrel through the lumen 162 of the second tubular body 154 and the lumen 186 of the of the catheter tip 180. The second tubular body 154 may be heated to at least approximately the glass transition temperature of the second tubular body 154. The distal edge 176 of the wide distal end 174 of the second tubular body 154 may be shaped so that the distal edge 176 is tapered. The shaping may take place during or after the heating process. The distal edge 176 may also be shaped so that it is rounded, blunt, rounded and tapered, or has any other shape known in the art.

The distal edge 176 of the second tubular body 154 may be shaped through any technique known in the art. One preferred method of shaping the distal edge 176 includes applying a compressive force to the wide distal end 174 of the second tubular body 154 to compress the wide distal end 174 of the second tubular body 154 around the catheter tip 180. A piece of Polytetrafluroethylene (PTFE) tubing may be suitable for applying the compressive force. The shaping may occur while the second tubular body 154 is being heated or after it is heated. Any technique for shaping known in the art may be used.

It may be desirable to thread a mandrel through the lumen 162 of the second tubular body 154 and the lumen 186 of the catheter tip 180 and heat the second tubular body 154 to at least approximately its glass transition temperature even when no shaping of the distal edge 176 occurs. This is because the second tubular body 154 will retain some memory of its original size and shape even after blow molded. When the second tubular body 154 is reheated with the catheter tip 180 disposed in the wide distal end 174 of the second tubular body 154, the second tubular body 154 may shrink around the catheter tip 180 due to its memory properties. The memory properties of the second tubular body 154 may cause it to shrink by as much as about 10% of its blow-molded size. This is desirable because it will increase the tightness of the fit between the catheter tip 180 and the second tubular body 154. This may further reduce the risk that the catheter tip 180 will become dislodged from the second tubular body 154 during use.

FIG. 3F illustrates a catheter tip assembly 196 with the addition of an outer catheter 200 having an inner diameter 202 that is approximately equal to the greatest outer diameter 170 of the blow molded portion of the section tubular body 154. As show in FIG. 3F, the second tubular body 154 may be positioned within the outer catheter 200 so that the distal edge 176 of the second tubular body 154 protrudes from the distal end 204 of the outer catheter 200.

Figure 5A:
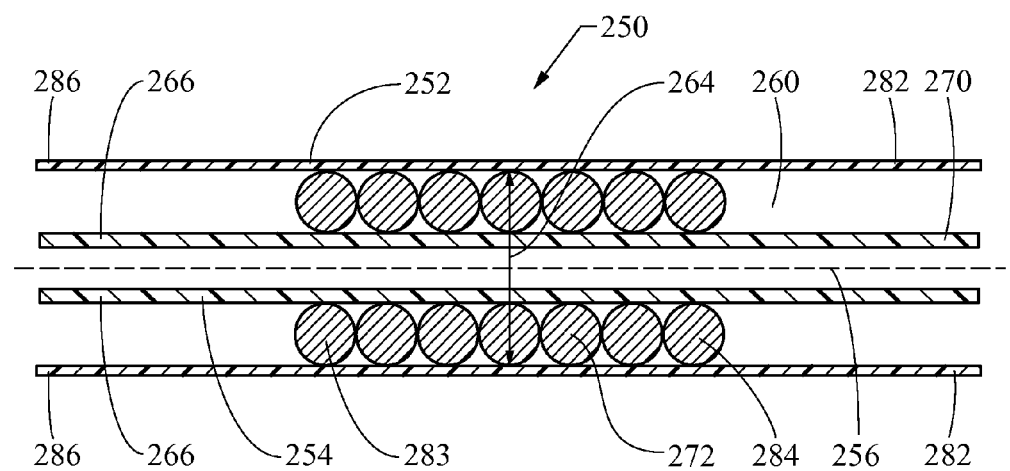
FIG. 5A is a partial side cross-sectional view of a blow-molding assembly.
Figure 5B:
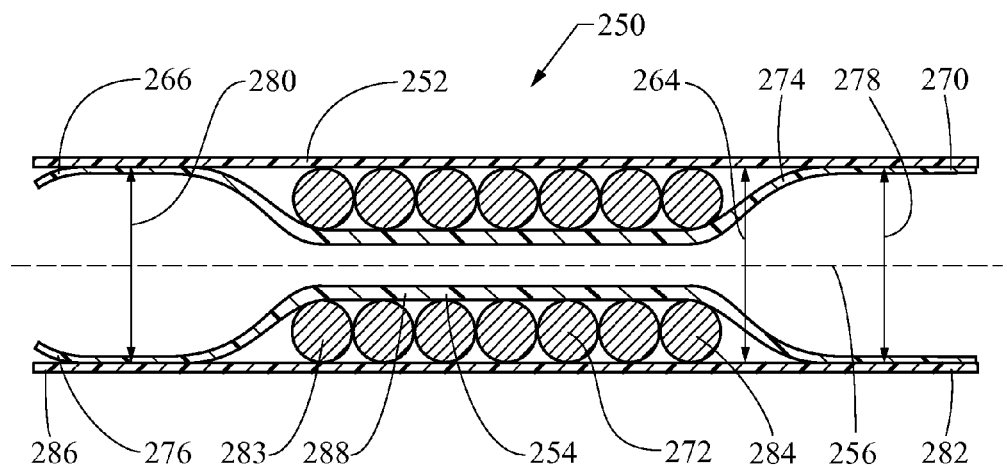
FIG. 5B is partial side cross-sectional view of the blow-molding assembly of FIG. 5A after blow molding.
Figure 5C:
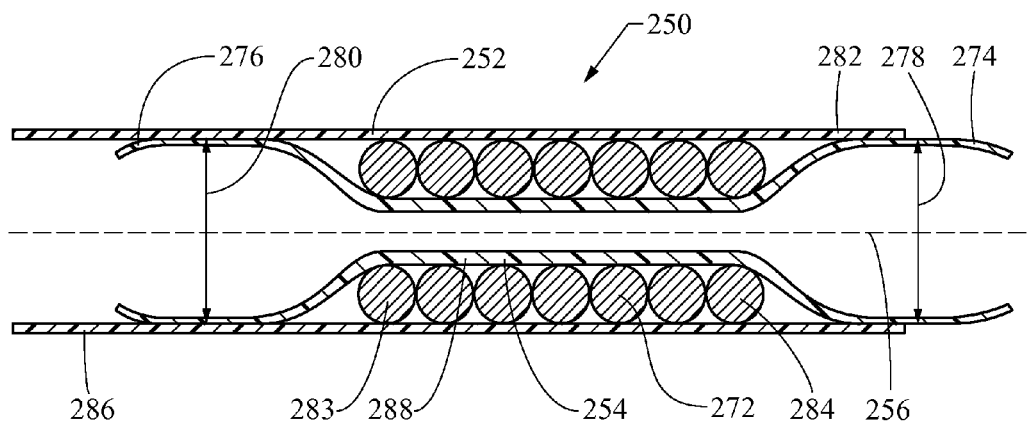
FIG. 5C is a partial side cross-sectional view of the blow-molding assembly of FIG. 5B.
Figure 5D:
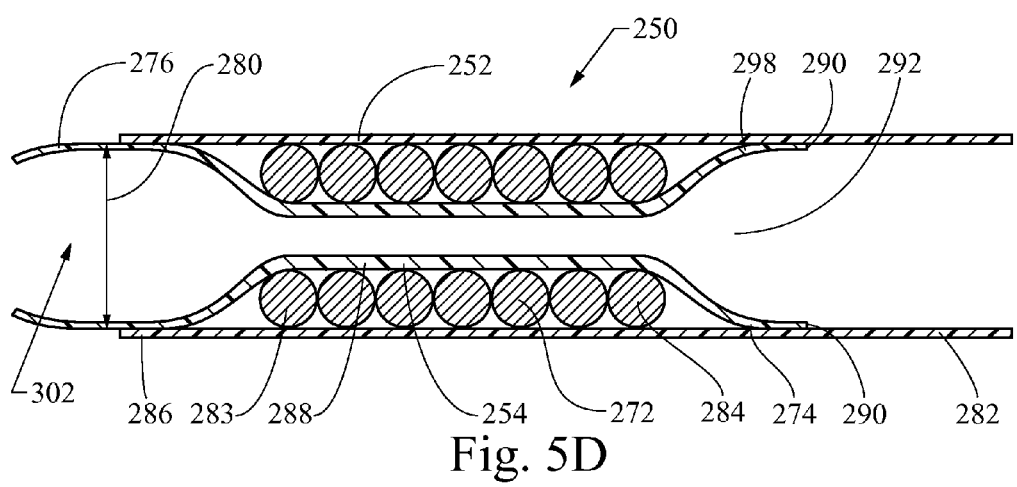
FIG. 5D is a partial side cross-sectional view of the blow-molding assembly of FIG. 5B.
Figure 5E:
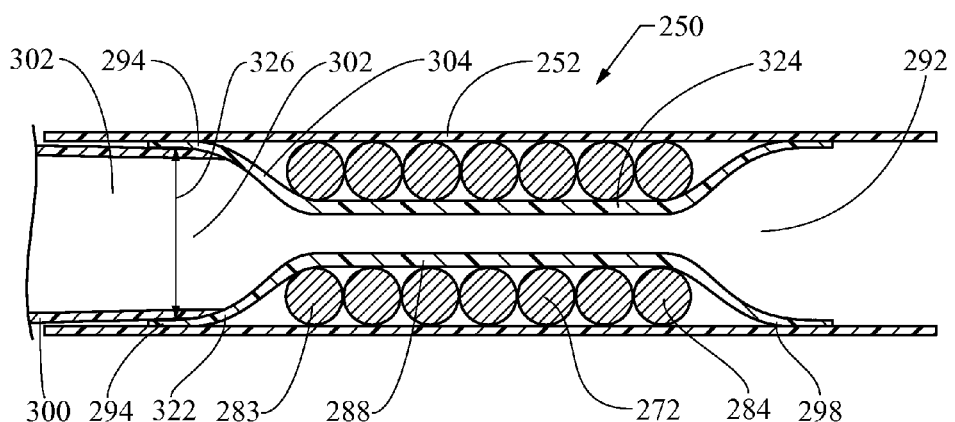
FIG. 5E is a partial side cross-sectional view of the blow-molding assembly of FIG. 5B with the addition of tubing.
Figure 5F:
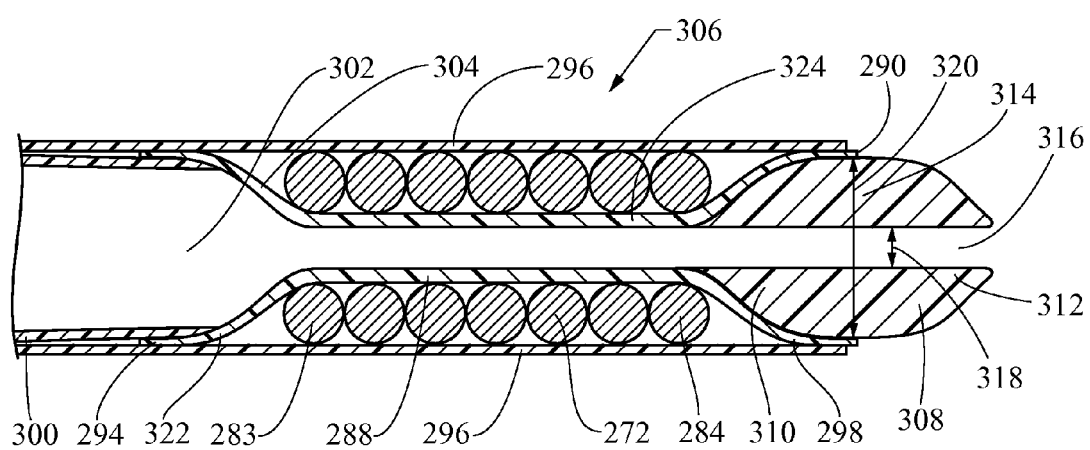
FIG. 5F is partial side cross-sectional view of a catheter tip assembly.
Figure 6:
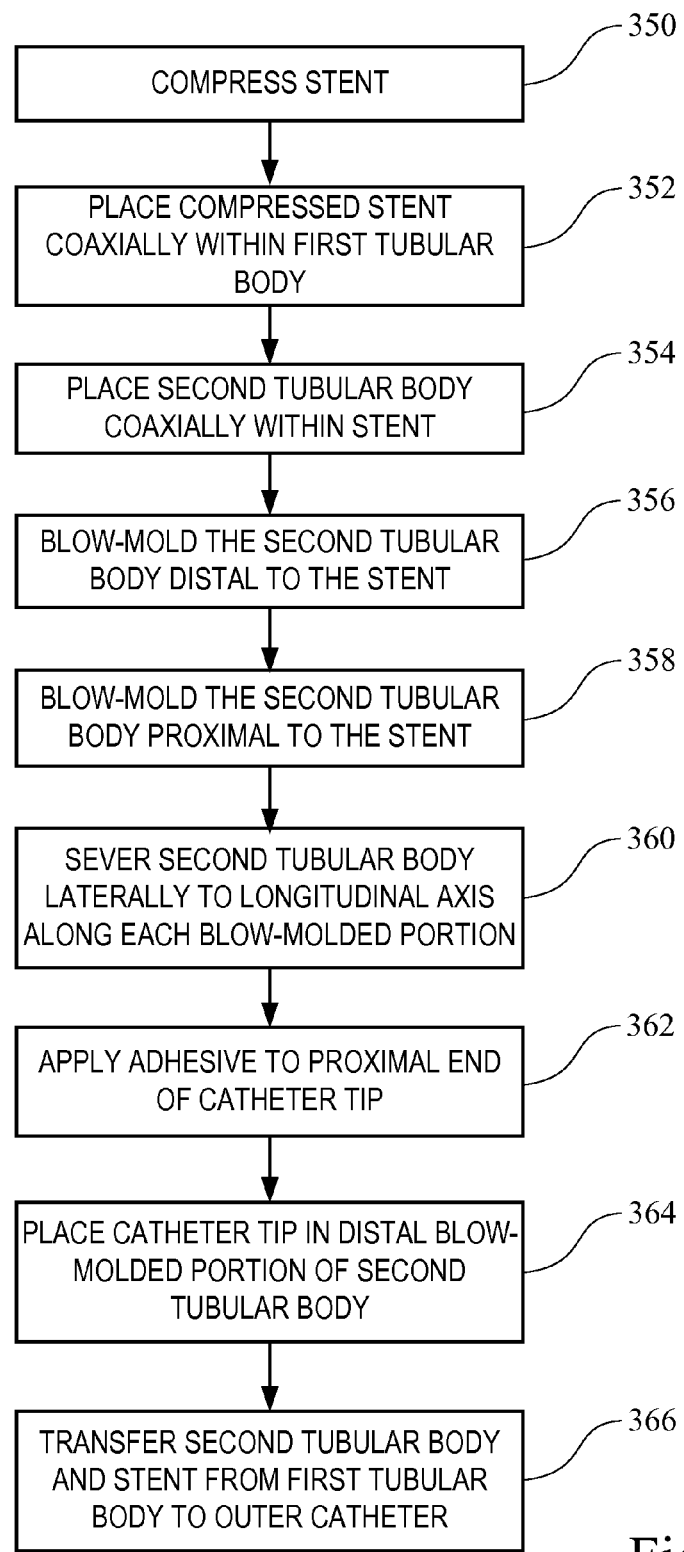
FIG. 6 illustrates an embodiment of a method for forming a catheter tip assembly with a stent loaded therein.

FIGS. 5A-F and 6 show a method for making a catheter tip assembly 306 with a compressed stent 272 pre-loaded on the inner catheter 324. FIG. 6 shows generally the steps of making a catheter tip assembly 306 with a stent pre-loaded. FIGS. 5A-F illustrate a blow molding assembly 250 and catheter tip assembly 306 during the process of making a catheter tip assembly 306. As set forth in FIG. 6, in one embodiment, a stent is compressed (Act 350) and placed coaxially within a first tubular body (Act 352). A second tubular body is placed coaxially within the stent (Act 354). The second tubular body is blow molded in two places: it is blow molded distal to the stent (Act 356) and it is blow molded proximal to the stent (Act 358). After blow molding, the second tubular body is severed laterally to its longitudinal axis along each blow-molded portion (Act 360). An adhesive is applied to the proximal end of a catheter tip (Act 362). The catheter tip is placed in the distal blow-molded portion of the second tubular body (Act 364). The second tubular body and stent are transferred from the first tubular body to an outer catheter (Act 366).

The order of the steps shown in FIG. 6 is exemplary only. In other embodiments, it may be possible to switch the order of several steps. For example, the blow molding of the distal and proximal sections of the second tubular body does not need to occur in any particular order relative to one another. The distal portion may be blow molded before proximal portion as shown in FIG. 6, after the proximal portion, or at the same time as the proximal portion. In addition, in some embodiments the second tubular body may be placed coaxially within the stent (Act 354) before the stent is compressed and placed coaxially within the first tubular body (Act 352). In addition, it is possible that each portion of the second tubular body may be severed laterally to the longitudinal axis of the second tubular body (Act 360) as each portion is blow molded. For example, a distal portion of the second tubular body could be blow molded (Act 356), severed (Act 360), and then the proximal portion of the second tubular body could be blow molded (Act 358) and severed (Act 360). In still other embodiments, the second tubular body and stent may be transferred from the first tubular body to the outer catheter (Act 366) before the catheter tip is placed in the distal blow-molded portion (Act 364). Any other suitable order of the steps known to a person of ordinary skill in the art may be used.

FIGS. 5A-F show in greater detail the method outlined in FIG. 6. The size and dimensions of the components of the blow-molding assembly 250 shown in FIG. 5A depend in part upon the size and dimensions of the catheter tip 308 shown in FIG. 5F. The catheter tip 308 has a tapered proximal end 310, an elongate center portion 314, and a tapered distal end 312. The catheter tip also has an inner diameter 318 that defines a lumen 316 and a greatest outer diameter 320.

The catheter tip assembly 250 of FIG. 5F may be made through the use of the blow-molding assembly 250 shown in FIG. 5A. As shown in FIG. 5A, a first tubular body 252 having a first end 282 and a second end 286 may be used. The first tubular body 252 has a longitudinal axis 256 and a lumen 260. The lumen 260 of the first tubular body defines an inner diameter 264 that is slightly greater than the greatest outer diameter 320 of the catheter tip 308 shown in FIG. 5F.

As further shown in FIG. 5A, a stent 272 having a distal end 284 and a proximal end 283 is compressed and placed coaxially within the first tubular body 252. The stent 272 is preferably shorter in length than the first tubular body 252. The stent is preferably positioned within the first tubular body 252 such that the first end 282 of the first tubular body 252 protrudes distally from the distal end 284 of the stent and the second end 286 of the first tubular body 252 protrudes proximally beyond the proximal end 283 of the stent 272.

In addition, FIG. 5A shows a second tubular body 254 comprised of a blow-moldable material placed coaxially within the compressed stent 272. The second tubular body 254 is longer than the stent 272. As shown in FIG. 5A, the second tubular body 254 is preferably positioned so that the first end 270 of the second tubular body 254 extends distally beyond the distal end 284 of the stent and the second end 266 of the second tubular body 254 extends proximally beyond the proximal end 283 of the stent 272. The second tubular body 254 and compressed stent 272 are preferably positioned within the first tubular body 252 so that the second tubular body 254 is at least approximately centered within the first tubular body 252.

Once the first tubular body 252, second tubular body 254 and stent 272 are positioned as shown in FIG. 5A, they may be blow molded as shown in FIG. 5B. As shown in FIG. 5B, two portions of the second tubular body 254 may be blow molded. A first portion 274 of the second tubular body 254 that is distal to the stent 272 may be blow molded until its greatest outer diameter 278 is at least approximately equal to the inner diameter 264 of the first tubular body 252. A second portion 276 of the second tubular body 254 that is proximal to the stent 272 may be blow molded until its greatest outer diameter 280 is at least approximately equal to the inner diameter 264 of the first tubular body 252. As shown in FIG. 5B, an elongate center portion 288 lies between the first blow molded portion 274 and the second blow molded portion 276.

By blow molding both a portion of the second tubular body 254 that is distal to the stent 272 (the first blow-molded portion 274) and a portion of the second tubular body 254 that is proximal to the stent 272 (the second blow molded portion 276), the stent is effectively "sandwiched" between the two blow-molded portions. It is preferable that there is no gap between the stent 272 and the blow-molded portions. This may prevent the formation of an undesirable gap between the proximal end 283 of the stent 272 and the stop member 304 in the finished loaded catheter tip assembly 306.

FIGS. 5C and 5D illustrate severing the second tubular body 254 once the blow molding is complete. As shown in FIGS. 5C and 5D, the first tubular body 252 is preferably slid longitudinally over the second tubular body 254 to expose each blow-molded portion. Each blow-molded portion may then be severed laterally to the longitudinal axis 256 to form a wide end. For example, FIG. 5C shows the first end 284 of the first tubular body 252 that has been slid in the proximal direction to expose the greatest outer diameter 278 of the first blow molded portion 274. The first molded portion may then be severed laterally to the longitudinal axis 256 to form a wide distal end 298 defining a lumen 292 and having a distal edge 290.

FIG. 5D shows the wide distal end 298 and distal edge 290 resulting from the severing of the first blow molded portion 274. FIG. 5D also shows the second end 280 of the first tubular body having been slid in the distal direction to expose the greatest outer diameter 288 of the second blow molded portion 276 of the second tubular body 254. The second blow molded portion 276 may then be severed laterally to the longitudinal axis 256 to form a wide proximal end 322 having a proximal edge 294. The wide proximal end 322 defines a lumen 302 having an inner diameter 326. The wide proximal end 322 and proximal edge 294 resulting from the severing of the second blow molded portion 294 is shown in FIG. 5E.

As shown in FIGS. 5C and 5D, each blow molded portion is preferably severed at or near its greatest outer diameter. This may be preferable because it allows for the widest possible distal and proximal end. However, the blow molded portions may be severed at any other desirable point. In addition, it is not necessary that the first tubular body 252 be slid to expose the second tubular body 254 before the second tubular body 254 is severed at the blow molded portions. In other embodiments, the first tubular body 252 may be cut away to expose the second tubular body 254. In still other embodiments, the first tubular body 252 may be severed along with the second tubular body 254. In embodiments wherein the first 252 and second tubular body 254 are simultaneously severed, it is preferable that the first tubular body 252 be composed of a transparent or semi-transparent material so that the widest point of each blow molded portion of the second tubular body 254 may be seen.

The blow-molded and severed second tubular body 254 shown in FIG. 5E is suitable for use as an inner catheter 324. FIG. 5E also shows the addition of tubing 300 suitable for insertion into a patient. A piece of tubing 300 with an outer diameter that is slightly less than the inner diameter 326 of the lumen 302 of the wide proximal end 322 may be attached to the wide proximal end 322 of the second tubular body 254. This may be accomplished by applying an adhesive to an exterior portion of the end of a piece of tubing 300. The end of the piece of tubing 300 may then be inserted into the lumen 302 of the wide proximal end 322 of the second tubular body 254. In other embodiments, the piece of tubing 300 may be attached by applying an adhesive to the interior of the piece of tubing 300 and sliding it over the outside of the wide proximal end 322 of the inner catheter 324. In still other embodiments, the piece of tubing may be attached via equivalent means known in the art such as interlocking pieces or a tight fit. In still other embodiments, the second blow molded portion 276 may not be severed and the second tubular body 254 may then be used in lieu of a separate piece of tubing 300.

FIG. 5F shows the addition of the catheter tip 308 and outer catheter 296 to form a catheter tip assembly 306. The catheter tip 308 may be attached by applying an adhesive to at least a portion of the tapered proximal end 310 of the catheter tip 308. The catheter tip 308 may then be placed into the lumen 292 of the wide distal end 298 of the inner catheter 324. Also, as shown in FIG. 5F, the stent 272 and blow-molded second tubular body 254 may be transferred from the first tubular body 252 to an outer catheter 296. The stent 272 is maintained in a compressed state as it is transferred from the first tubular body 252 into the outer catheter 296. Thus, the first tubular body 252 functions as a transfer tube. The outer catheter 296 is also commonly called a sheath.

Additional modifications and blow molding may be used to further shape the inner catheter 324, particularly the distal edge 290 of the inner catheter 324. Several of such modifications are described in relation to FIG. 3E. These modifications are preferably made after the addition of the catheter tip 308, but before the inner catheter 324 is transferred from the first tubular body 252 to the outer catheter 296. This is because the first tubular body 252 is typically not blow-moldable and thus suitable for retaining the stent 272 in the compressed position as portions of the inner catheter 324 are shaped via blow molding and other forces. In contrast, many of the materials that are particularly advantageous for use as an outer catheter may not hold their shape well as the inner catheter 324 is blow molded or shaped.

The catheter tip assembly 306 formed by the method shown in FIGS. 5A-F has an inner catheter 324 with a wide distal end 298 and a wide proximal end 322. The wide proximal end 322 forms an integral stop member 304. This may be particularly advantageous because the stop member 304 is custom-formed to fit around the stent 272 and thus eliminates any undesirable gap between the proximal end 282 of the stent 272 and the stop member 304.

When using the method shown in FIGS. 5A-F to make a catheter tip assembly 306, it is preferable that the temperature, pressure and duration of the blow molding are tailored to allow the center elongate portion 288 of the second tubular body 254 to become blow molded to conform to the size of the inner diameter of the compressed stent 272, but not to seep into the crevices between the various struts, rings, and connections members of the stent 272. It is preferable that the second tubular body 254 is not blow molded into the cracks and crevices of the stent 272 because this might prevent the stent 272 expanding properly once inserted. In addition, the protrusions formed by blow molding the second tubular body 254 into the cracks and crevices of the stent might snag or catch the stent as the second tubular body 254 is withdrawn during use. For embodiments using a PET second tubular body, applying steam at 212° F. and pressure at 50 psi may be suitable for producing the desired amount of blow molding.

In some embodiments according to the methods shown in FIGS. 3A-F, 4, and 5A-F, it may be desirable to combine blow molding with other techniques in order to obtain the thinnest possible wide distal end of the inner catheter. For example, all or part of the portion of the second tubular body that will form the wide distal end via blow molding may be thinned prior to blow molding. The portion of the second tubular body destined to become the elongate center portion of the inner catheter and the proximal portion of the elongate catheter would not be thinned. After blow molding, the blow-molded portion will be even less thick than it would have been without the thinning. However, the non-blow-molded portion will maintain its original thickness. Thinning may be advantageous because a very thin-walled wide distal end may be obtained without sacrificing any of the strength of the elongate center portion of the inner catheter. Thinning may be accomplished by removing material from the interior of the second tubular body, by e.g. machining, drilling, or any other technique known in the art.

The first tubular body may be made of any material having a higher glass transition temperature than the second tubular body. For example, PTFE and fluorinated ethylene-propylene (FEP) may be suitable materials to use for the first tubular body for many embodiments. However, any other material suitable for blow molding known in the art may be used.

In one preferred embodiment, the first tubular body is formed of PTFE and the second tubular body is formed of PET. After the second tubular body is inserted into the first tubular body, the second tubular body is sealed and pressurized air is blown into the second tubular body. The pressurized air is preferably 50 psi. Heat is applied to a portion of the second tubular body through the use of hot steam at about 212° F., which is greater than the glass transition temperature of PET. As pressure and heat are applied, the second tubular body balloons outwardly to form a wide portion. This wide portion may be severed to form an inner catheter having a wide distal end.

In other embodiments, the pressure of the gas used during blow molding may range between 30 psi and 90 psi. The heat applied during blow molding may range between 200° F. and 280° F. Specifically, pressure may range between 35 psi and 45 psi and the heat may range between 210° F. and 220° F. In other embodiments, the pressure may range between 85 psi and 95 psi and the heat may range between 230° F. and 280° F. By adjusting the pressure, temperature, or a combination thereof, it is possible to control the shape and thickness of the blow-molded portion of the second tubular body. The heat may be applied through the use of hot steam, hot air (via a hot air gun), or through any other technique know known in the art. Likewise, pressurized air may be applied through the use of any technique known in the art.

It may be advantageous to utilize a blow molding technique to make an inner catheter for the catheter tip assembly because blow molding will allow the diameter of the wide distal end of the inner catheter to expand up to about five times wider than the diameter of the narrow elongate portion of the inner catheter. In addition, as the inner catheter is blow molded, the thickness of the tubular body forming the blow molded-portion will naturally become thinner than the non-blow-molded portion. This minimizes the additional overall width of the catheter tip assembly attributable to the inner catheter.

The catheter tip assembly is particularly suitable for the insertion of stents into the blood vessels of a patient. The catheter tip assembly is preferably used for the insertion of a self-expanding stent. However, the catheter tip assembly may also be used with balloon-expandable stents. In addition, the catheter tip assembly may be used for the insertion of stent grafts. The size of the components of the catheter tip assembly may be adjusted to accommodate different sizes and styles of stents. Although the catheter tip assembly is particularly suitable for the insertion of stents, a person skilled in the art would understand how to adapt it for other medical procedures.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A method for making a catheter tip assembly comprising:
   providing a catheter tip having an inner diameter defining a lumen and a greatest outer diameter, said catheter tip having a tapered proximal end, an elongate center portion, and a tapered distal end;

providing a first tubular body having a longitudinal axis, and an inner diameter slightly greater than said greatest outer diameter of said catheter tip;

placing a second tubular body coaxially within said first tubular body, said second tubular body having an inner diameter defining a lumen and an outer diameter;

positioning said second tubular body within said first tubular body so that said second tubular body is at least approximately centered within said first tubular body;

blow molding a portion of said second tubular body until a greatest outer diameter of said blow-molded portion of said second tubular body is approximately equal to said inner diameter of said first tubular body;

removing said second tubular body from said first tubular body;

severing said second tubular body laterally to said longitudinal axis along said blow-molded portion, thereby forming a narrow elongate portion and a blow-molded wide distal end having a distal edge;

applying an adhesive to said tapered proximal end of said catheter tip; and placing said catheter tip into said lumen of said wide distal end of said second tubular body.

2. The method for making a catheter tip assembly of claim 1 further comprising:

threading a mandrel through said lumen of said second tubular body and said lumen of said catheter tip; and heating said second tubular body to at least approximately the glass transition temperature of said second tubular body.

3. The method for making a catheter tip assembly of claim 2 further comprising shaping said distal edge of said wide distal end so that said distal edge is tapered.

4. The method for making a catheter tip assembly of claim 3 wherein said heating and shaping occur generally simultaneously.

5. The method for making a catheter tip assembly of claim 1 further comprising applying a compressive force to said wide distal end of said second tubular body, thereby compressing said wide distal end around said catheter tip.

6. The method for making a catheter tip assembly of claim 1 wherein said second tubular body is severed at approximately said greatest outer diameter of said blow-molded portion of said second tubular body.

7. The method of making a catheter tip assembly of claim 1 further comprising thinning a portion of said second tubular body prior to blow molding.

8. The method for making a catheter tip assembly of claim 1, wherein said blow molding comprises:

sealing an end of said second tubular body;

blowing pressurized air through said second tubular body;

heating a portion of said second tubular body to a temperature at least approximately the glass transition temperature of said second tubular body; and allowing said second tubular body to cool.

9. A method for making a catheter tip assembly comprising:

providing a catheter tip having an inner diameter defining a lumen and a greatest outer diameter, said catheter tip having a tapered proximal end, an elongate center portion, and a tapered distal end;

providing a first tubular body having a longitudinal axis, and an inner diameter slightly greater than said greatest outer diameter of said catheter tip;

compressing a stent having a distal end and a proximal end, said stent being shorter than said first tubular body;

placing said compressed stent coaxially within said first tubular body;

placing a second tubular body comprised of a blow-moldable material coaxially within said stent, said second tubular body being longer than said stent;

positioning said second tubular body and said compressed stent within said first tubular body so that said second tubular body is at least approximately centered within said first tubular body;

blow molding a first portion of said second tubular body that is distal to said stent until a greatest outer diameter of said blow-molded first portion of said second tubular body is at least approximately equal to said inner diameter of said first tubular body;

blow molding a second portion of said second tubular body that is proximal to said stent until a greatest outer diameter of said blow-molded second portion of said second tubular body is at least approximately equal to said inner diameter of said first tubular body;

severing said second tubular body laterally to said longitudinal axis along said first blow-molded portion, thereby forming a blow-molded wide distal end having a distal edge, said wide distal end defining a lumen;

severing said second tubular body laterally to said longitudinal axis along said second blow-molded portion, thereby forming a blow-molded wide proximal end having a proximal edge, said wide proximal end defining a lumen having a second inner diameter;

transferring said stent and said blow-molded second tubular body from said first tubular body into an outer catheter;

maintaining said stent in a compressed state as it is transferred from said first tubular body into said outer catheter;

applying an adhesive to at least a portion of said tapered proximal end of said catheter tip;

placing said catheter tip into said lumen of said wide distal end of said second tubular body;

applying adhesive to an exterior portion of an end of a piece of tubing, said piece of tubing having an outer diameter that is slightly less than said inner diameter of said lumen of said wide proximal end of said second tubular body; and inserting said end of said piece of tubing into said lumen of said wide proximal end of said second tubular body.

* * * * *

UNITED STATES PATENT AND TRADEMARK OFFICE
CERTIFICATE OF CORRECTION

PATENT NO. : 8,597,454 B2  Page 1 of 1
APPLICATION NO. : 13/063422
DATED : December 3, 2013
INVENTOR(S) : Parker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 284 days.

Signed and Sealed this
Twenty-second Day of September, 2015

Michelle K. Lee
*Director of the United States Patent and Trademark Office*